United States Patent [19]

Fuller et al.

[11] Patent Number: 4,464,122

[45] Date of Patent: Aug. 7, 1984

[54] HEALTH POTENTIAL SUMMARY AND INCENTIVE SYSTEM

[76] Inventors: Berkeley Fuller, 1025 Wilder Ave., Honolulu, Hi. 96813; Linda Soll, 606 Hunakai St., Honolulu, Hi. 96816; Margretta Obrecht, 47-262A Hui Iwa St., Kaneohe, Hi. 96744; Gary Poole, Box 8637, PSSA, Auckland 3, New Zealand; Edward F. Campbell, Jr., 55 S. Judd St. #806, Honolulu, Hi. 96817; Margaret Parsons, 2144 Haena Dr., Honolulu, Hi. 96813; Valerie P. P. Chun, 2612A, Kapiolani Blvd., Honolulu, Hi. 96826; David R. Shearer, 2452 Tusitala, #710, Honolulu, Hi. 96815; Thomas M. Cashman, 3130 Huelani Dr., Honolulu, Hi. 96814

[21] Appl. No.: 446,344

[22] Filed: Dec. 2, 1982

[51] Int. Cl.³ ............................................. G09B 19/00
[52] U.S. Cl. ................................... 434/262; 128/630; 283/1 A; 434/127
[58] Field of Search ............... 434/319, 320, 321, 322, 434/262, 127; 128/630; 283/1 A, 56

[56] References Cited

U.S. PATENT DOCUMENTS 3,407,513 10/1968 Conn ................................. 434/363
3,708,891 1/1973 Rosov ............................... 434/321

OTHER PUBLICATIONS

"Health 80's for Hospitals" ©1980, by Medical Datamation.
"Your Personal Health Report" by The Institute for Personal Health ©1980.
"Personal Risk Profile" by General Health, Inc. ©1983.

Primary Examiner—William H. Grieb
Attorney, Agent, or Firm—Beehler, Pavitt, Siegemund, Jagger & Martella

[57] ABSTRACT

A health potential study and summary makes use of a multiple-page, relatively comprehensive, questionnaire for the individual, an analysis of answers to the questionnaire in readable summary form and an abbreviated life-style resume of the analysis coupled with a visually graphic portrayal of health potential on a graduated scale. The questionnaire is divided into different categories of health affecting subjects arranged so that answers in the form of yes, no, unanswered, or degree rated against a specified rate scale, are placed in a score box adjacent the question. The questionnaire includes an actual food intake diary for a specified period of days and an exercise report. The analysis and appropriate comments are presented in printed form for the respective categories in a manner comparing ideal conditions against actual conditions of the individual where prevailing conditions are picked from the score boxes and commentary and recommendations selected from a data bank according to score. The resume is a printed, color accented, numerically comparative box score showing how the health rating of the subject in the respective categories compares with rating levels portrayed respectively at levels identified as recommended, elevated or risk, and accompanied by a final health incentive feature wherein the actual age of the subject is compared with his age as appraised by the summary and a relative age achievable by compliance with the recommendations.

14 Claims, 16 Drawing Figures

Fig. 2.

PART I: HEALTH APPRAISAL QUESTIONS

● DIRECTIONS: Please check the box for each item that describes you best. (If you are under 20 or over 74 please skip Part I and start your Questionnaire with Part II.)

1. Your SEX is ................................................................. MALE ☐
    FEMALE ☐

2. Your race/ETHNIC ORIGIN is: .................................... WHITE (non-Hispanic) ☐
    ASIAN OR PACIFIC ISLANDER ☐
    BLACK (non-Hispanic) ☐
    AMERICAN INDIAN OR ALASKAN NATIVE ☐
    HISPANIC ☐
    NOT SURE ☐

3. Your AGE (at last birthday): ........................................................ (Years Old) ☐

4. Your HEIGHT (without shoes) is: ........................................ Feet ☐ Inches ☐

5. Your WEIGHT (without shoes) is: ........................................ Pounds ☐

6. About your TOBACCO USAGE: .......................................... I am a smoker ☐
    I am an ex-smoker ☐
    FOR SMOKERS & EX-SMOKERS:
    Please fill in average numbers smoked per day for last five years     I have never smoked ☐
    (ex-smokers should use last five years before quitting):     Cigarettes per day ☐
    Pipes/Cigars per day (smoke inhaled) ☐
    EX-SMOKERS ONLY:     Pipes/Cigars per day  (NOT inhaled) ☐
    Enter Number of years stopped smoking
    (Note: Enter "1" for less than one year) ........................................................ ☐

7. About your ALCOHOL USAGE: .................... I sometimes drink alcoholic beverages ☐
    I am an ex-drinker (I stopped) ☐
    IF YOU DRINK ALCOHOL, enter     I am a non-drinker (less than 1 per wk) ☐
    average number of drinks per week:     Bottles beer per week ☐
    Glasses wine per week ☐
    1 Drink = 12-oz beer, 4-oz wine or
    1½ oz distilled beverage.     Mixed drinks or shots of liquor per week ☐

---

19. Considering your age, how would
    you describe your overall physical health?    EXCELLENT ☐
    GOOD ☐
    FAIR ☐
    POOR ☐

20. In general, how satisfied are you with your life?    MOSTLY SATISFIED ☐
    PARTLY SATISFIED ☐
    MOSTLY DISAPPOINTED ☐
    NOT SURE ☐

21. In general how strong are your social ties with family and friends?    VERY STRONG ☐
    ABOUT AVERAGE ☐
    WEAKER THAN AVERAGE ☐
    NOT SURE ☐

22. How many hours sleep do you usually get every night?    6 Hours or Less ☐
    7 Hours ☐
    8 Hours ☐
    9 Hours or more ☐

*Fig. 3.*

PART II: STRESS INFORMATION

- The following questions relate to stress. Here are some simple but important points to keep in mind when completing this section of the questionnaire:
  1. Do not spend too much time thinking about your answers. Just give the first, natural answer that comes to you and then move on to the next item.
  2. Answer as honestly as you can what is true for YOU. Please do not mark something because it seems like the "right thing to say."
  3. Answer EVERY item, even if it does not seem to apply to you very well.
  4. Please give only ONE response for each item.

Below is a list of life events which may happen to anyone at some time or another. For each event listed, check whether that event DID or DID NOT occur in your life within the past 1 year (12 months). If the event occurred longer than 12 months ago, you would indicate it DID NOT occur.

|  | Did occur | Did not occur |
|---|---|---|
| Death of a spouse | ☐ | ☐ |
| Divorce | ☐ | ☐ |
| Marital separation | ☐ | ☐ |
| Death of close family member | ☐ | ☐ |
| Marital reconciliation | ☐ | ☐ |
| Change in number of arguments with spouse | ☐ | ☐ |
| Son or daughter leaving home | ☐ | ☐ |
| Trouble with in-laws | ☐ | ☐ |
| Spouse begins or stops work | ☐ | ☐ |
| Change in number of family get-togethers | ☐ | ☐ |
| Minor violation | ☐ | ☐ |
| Jail term | ☐ | ☐ |
| Personal injury or illness | ☐ | ☐ |
| Any change in sleeping habits | ☐ | ☐ |
| Any change in eating habits | ☐ | ☐ |

- Make a brief and honest evaluation of how you are feeling right NOW—that is—how you feel TODAY. Please select an answer from the choices below that best describes how you feel currently and write the number representing it in the box next to the statement. Just select the answer that first comes into your mind.

HOW MUCH IS IT TRUE FOR YOU? (NOW, TODAY)

1—NOT AT ALL   3—MODERATELY SO
  2—SOMEWHAT   4—VERY MUCH SO

I feel calm ............ ☐
  I feel secure ............ ☐
  I am tense ............ ☐
  I feel regretful ............ ☐
  I am at ease ............ ☐
  I feel upset ............ ☐
  I am presently worrying over possible misfortunes ............ ☐
  I feel rested ............ ☐

Fig. 4.

PART III: EXERCISE DATA

● Circle the number next to any LEISURE TIME exercise activity you actively engaged in during the LAST TWO WEEKS (counting backwards 14 days from today.)

For each activity you circled, fill in the number of times you engaged in it in the TWO WEEK period.

For each activity you circled, estimate the average length of time you spent doing it.

EXAMPLE  (1) Calisthenics (stretching only) ....... [3]  30 min.

1 Calisthenics (stretching only)
2 Yoga
3 Bicycling
4 Dancing, Country & Western
5 Dancing, Disco
6 Dancing, vigorous Ballroom
7 Golf (walking only)
8 Jogging/Running
9 Mini-trampoline
10 Rope jumping
11 Skating
12 Tennis (singles)
13 Walking
14 Waterskiing 20 Dancing, Modern Dance
21 Basketball
22 Handball
23 Paddleball
24 Raquetball
25 Squash
26 Swimming
27 Snow skiing
28 Dancing, Jazz
29 Jazzercise, Dancergetics
30 Sports Conditioning
31 _____ other

PART IV: NUTRITION ANALYSIS

ESTIMATE the number of times PER DAY, PER WEEK or PER MONTH that you eat a serving of EACH of the list of foods below. Serving sizes are shown in parentheses with each item. If you NEVER or RARELY eat the food listed indicate N (Never) or R (Rarely).

EXAMPLE A: If you never eat cereals, but do usually have two slices of white enriched toast with breakfast, and one roll with dinner, for the appropriate item below you would mark:

Enriched cereals, bread, rolls _____3_____ Times per ⃝DAY⃝/WEEK/MONTH

EXAMPLE B: If you usually add one teaspoon of sugar to your morning coffee, and two teaspoons of jelly or honey to your breakfast toast, for the appropriate item below you would mark:

Number teaspoons Sugar added to cereal, fruit, coffee, toast, etc. _____3_____ Times per ⃝DAY⃝/WEEK/MONTH

ESTIMATE your use of the following foods (serving sizes indicated), and circle whether your answer is "per DAY," "per WEEK" or "per MONTH" for each:

Eggs (1) _____ Times per: DAY/WEEK/MONTH
Liver, kidney, brains (3 oz) _____ Times per: DAY/WEEK/MONTH
Shellfish: Shrimp, crayfish, lobster, crab, etc. (3 oz.) _____ Times per: DAY/WEEK/MONTH Beef, Pork, Lamb (3 oz) _____ Times per: DAY/WEEK/MONTH
Butter (1 pat = 1½ t.) _____ Times per: DAY/WEEK/MONTH
Whole milk (1 cup) _____ Times per: DAY/WEEK/MONTH 2% milk (1 cup) _____ Times per: DAY/WEEK/MONTH
Skim milk (1 cup) _____ Times per: DAY/WEEK/MONTH
Cream (1 T.) _____ Times per: DAY/WEEK/MONTH Gravies (1 T.) _____ Times per: DAY/WEEK/MONTH
Ice cream (½ cup) _____ Times per: DAY/WEEK/MONTH
Cheese: Cheddar, jack, etc. (1 oz) _____ Times per: DAY/WEEK/MONTH Yogurt (1 cup) _____ Times per: DAY/WEEK/MONTH
Cottage cheese (½ cup) _____ Times per: DAY/WEEK/MONTH
Cakes—1 piece, 2" × 2" × 2" _____ Times per: DAY/WEEK/MONTH Pastries, pie slice (1) _____ Times per: DAY/WEEK/MONTH
Cookies (1) _____ Times per: DAY/WEEK/MONTH
Soda pop—regular, diet (12 oz) _____ Times per: DAY/WEEK/MONTH Candy (3-1" pieces or 1 candy bar) _____ Times per: DAY/WEEK/MONTH
Margarine (1 pat = 1½ t.) _____ Times per: DAY/WEEK/MONTH
Vegetable oils (1 t.) _____ Times per: DAY/WEEK/MONTH Nuts, seeds, peanut butter (1 oz = 2 T.) _____ Times per: DAY/WEEK/MONTH
Olives, pickles (1 3" pickle or 3 olives ) _____ Times per: DAY/WEEK/MONTH
Smoked or canned fish (3 oz) _____ Times per: DAY/WEEK/MONTH

Fig. 6.

FOOD DIARY
DAY 1

| Time | Place | Foods & Beverages | Method of Preparation | Amount |
|---|---|---|---|---|
| 6:15 am | home, kitchen | pancake<br>strawberry syrup | stove top baked in a griddle<br>strawberries cooked in sugar syrup | 1, 4" diameter<br>¼ cup |
| | | pork link sausage<br>orange juice | fried<br>frozen (100% unsweet.) | 2 3" long<br>¾ cup |
| 11:30 am | Cafeteria | egg sandwich<br>hamburger bun baked (white)<br>egg<br>mayonaise<br>relish<br>lettuce<br>fruit punch (syrup + water) | | 1 4" diameter<br>1 med. egg<br>1 tablespoon<br>1 teaspoon<br>1 med. leaf<br>½ cup |

*Fig. 7ᵃ*

Your Health Potential Summary
RECOMMENDATIONS

I. NUTRITION

Listed in the table, below, are the most recent Recommended Dietary Allowances (RDA's) or U.S. Dietary Guideline recommendations. The extreme right-hand column shows how much of these various nutrients you are presently consuming in your diet (based on the food record you provided for this report).

An asterisk beside one of your data entries indicates a deficiency, which you can correct by following the specific suggestions listed in the following recommendations section.

| Nutrient | Measurement Unit | Recommended Amount MALE | FEMALE | YOUR Average Daily Consumption |
|---|---|---|---|---|
| Total Fat | Gram | — | — | 85.7 |
| Saturated Fat | Gram | — | — | 50.6 |
| Polyunsaturated Fat | Gram | — | — | 16.0 |
| Dietary Cholesterol | mg. | 300 | 300 | 915 |
| Calories | Kilocalories | — | — | 1387 |
| Protein | Gram | 56 | 44 | 97 |
| Vitamin A | I.U. | 5,000 | 4,000 | 4308 * |
| Vitamin C | mg. | 60 | 60 | 58 * |
| Niacin | mg. | 18 | 13 | 18.7 |
| Thiamin (B₁) | mg. | 1.4 | 1.0 | 1.9 |
| Riboflavin | mg. | 1.6 | 1.2 | 1.2 * |
| Calcium | mg. | 800 | 800 | 281 * |
| Iron | mg. | 10 | 18 | 13.8 |
| Salt | Gram | 5 | 5 | 2.3 |

Fig. 7b

● Fat Consumption

Approximately 42 percent of the calories in the average American diet come from fat. This high fat consumption has been associated with increased incidence of heart and blood vessel disease, and, more recently, with several forms of cancer. The United States Dietary Guidelines recommend a reduction of fat intake to approximately 30 percent of calories.

The type of fat you eat is also significant. High saturated (mainly from animal products) fat diets increase blood cholesterol levels and the risk of heart and blood vessel disease. It is recommended that saturated (mainly animal) and polyunsaturated (mainly vegetable) fat be approximately equally represented in your diet so that the combined amount remains under 30 percent of calories.

Your total intake averaged 85.7 grams per day or 55% of your calories. In order to maintain fat consumption near 30% of calories we recommend selecting more entrees from fish, poultry, and cooked dry beans (as in lentil soup or tostadas) while reducing your intake of beef, lamb and pork.

The above substitutions will both reduce the total fat and the saturated fat in your diet, as well as the dietary cholesterol. We commend that you avoid liver and organ meats and restrict your use of eggs and shrimp (all high in dietary cholesterol). Other suggestions which can bring your polyunsaturated-to-saturated fat ratio to approximately 1:1 include substituting oil in place of shortening in cooking, verifying that your margarine is high in polyunsaturates (with liquid oil listed as the first ingredient), and trying a 1% fat or skim milk where you now use 2% fat milk. These suggestions should be significant in making the slight reduction necessary to bring your serum cholesterol level under 220 mg/dl where we see decreased risks for heart disease.

● Percent Body Fat

Overweight is approaching epidemic proportions in the United States. The measurement of your "percent body fat" indicates whether excess weight you may have is being carried as adipose (fat) tissue, or as muscle. If your percent body fat is above the recommended level, you have more than an average amount of body fat.

● Your Nutrition Recommendations:

Your weight is above the ideal range for your height and your percent body fat exceeds the recommended level. To reduce body fat and decrease risk for chronic disease, we recommend combining the suggested dietary modifications with an on-going cardiovascular exercise program.

Fig. 7.C1

● Vitamins & Minerals

Vitamins are necessary in small amounts for normal growth, maintenance of health, and reproduction. Vitamin consumption in excess of the RDA requirement will simply be excreted by your body, except in the case of fat-soluble vitamins, such as Vitamin A, which taken in large doses, can accumulate to toxic levels.

Minerals have two main functions in the body: *building* skeletal and soft tissue and *regulating* body functions as blood clotting, heartbeat, and transport of oxygen. While minerals are essential in the recommended amounts, some can cause adverse health effects in megadoses.

● Salt Intake

Table salt, or sodium chloride, contains about 40 percent sodium. Sodium has been identified as a dietary factor in high blood pressure (hypertension). Reduced sodium intake is important in treating, and possibly even in preventing hypertension, which is associated with increased risk for heart disease and stroke.

Your high fat diet contributes to the identified nutrient deficiencies in vitamins A and C, riboflavin and calcium. Depending on your choice of one dark green leafy vegetable and one other vegetable daily, your fat-soluble vitamin A intake may actually be adequate. However, only three fruit servings per week can produce borderline vitamin C deficiency. An additional daily serving of one of these fruits and vegetables high in both vitamins A and C will provide adequate intake of both nutrients: broccoli, spinach, tomato, papaya, mango, and cantaloupe.

Your deficiency in riboflavin and calcium can be eliminated by increasing your servings of milk from 3 times per week to daily use.

The sodium equivalent of salt content of your food alone was excellent at approximately one half the recommended 5 grams per day. The use of salt in cooking your food and your use of salt at the table increase this amount to an unknown extent. We recommend keeping the addition of salt and shoyu to your food to the lowest level that is comfortable for you.

Fig. 8.

II. EXERCISE

The muscular physique which symbolizes Physical Fitness in the 30's and 40's is only one part (muscular function) of the concept of "Total Fitness" we have today. To be considered "totally fit" today, you must have a minimum amount of not only *muscular function* (muscular strength, endurance, power, coordination, etc.) but also *cardiovascular endurance* (the ability to maintain "vigorous" physical activity which trains the heart) and *flexibility*. In addition, *normal body weight* is frequently included as part of "total fitness," since exercise plays a vital role in normalizing body weight and body fat. This portion of your Health Potential Summary reviews all of these "fitness components."

● Flexibility

Maintenance of adequate flexibility (through stretching exercise) has been found extremely helpful in relieving tension, back and joint pain, and in improving your appearance through improved posture. To obtain these benefits, it is recommended that stretching types of exercise such as yoga, dance stretches, stretching calisthenics (which include some toe touching, side bending, and twisting of the trunk), be done at least every other day for approximately 10 minutes per time.

● Cardiovascular Endurance

A 1981 study has reported that British office workers who engage in some "vigorous" exercise (such as brisk walking, jogging, etc.) develop 50 percent less heart disease than their sedentary counterparts.

For a strong, efficient heart, the recommended amount of this type of exercise is a minimum of 20 minutes of activity a minimum of 3 times per week. Recommended activities include:

jogging                                           skating
brisk walking (including walking a golf course)   singles tennis
basketball                                        raquetball
bicycling                                         handball
vigorous dancing (including disco and aerobic)    squash
rope and mini-trampoline jumping                  swimming
stair climbing                                    sports conditioning ● Your Recommendations:

You indicated that you stretch an average of 1-1/2 times a week for approximately 10 minutes per time.

We congratulate you for these efforts, but suggest that an increase to the recommended amount would be extremely beneficial.

You indicated that you golf an average of less than once a week for approximately 2 hours per time and that you also walk once a week for approximately 30 minutes per time.

We congratulate you for these efforts, but suggest that an increase in the number of exercise sessions to the recommended amount would be extremely beneficial.

Fig. 9.

III. CONSUMPTION OF ALCOHOL, TOBACCO, DRUGS

People in our society have gotten into the habit of overconsuming, and relying on a very large variety of substances that affect our minds and bodies in various ways. Much of this overuse of mood-altering substances is motivated by attempts to alleviate, escape from, or at least mask, the effects of stress. Unfortunately, over-reliance and overuse of substances such as alcohol, prescription and non-prescription mood-changers (such as tranquilizers and "uppers")—itself causes its own physical and emotional stress reactions. Thus the behavior (over-relying on mind-affecting substances), initially sought to relieve stress, actually increases that stress.

● *A CAUTION*

Tobacco is NO exception to "substance-overuse." Research has linked cancer, heart disease and other chronic diseases to tobacco consumption. NO BENEFITS ARE ASSOCIATED WITH THE CONSUMPTION OF TOBACCO.

Your "Health Potential Summary" signal sheet section on Alcohol, Tobacco and Drugs indicates to you where you stand as an avoider, too-frequent user, or abuser of these substances. It is very important for you to notice if you have "drifted into" overusing these substances to handle stress. You can learn other, more successful and less harmful techniques for managing stress.

If you are having problems with smoking or drugs, see your physician. YOU CAN DECREASE OR STOP YOUR CONSUMPTION.

● Your Use-of-Substances Recommendations:

Congratulations on being a non-smoker! Your decision to avoid the use of tobacco will add years to your life expectancy and help you stay in good health on a daily basis.

Your present use of alcohol, as reported on the questionnaire, is within a moderately excessive range. Research has indicated that there is some long-term risk within this range for liver disease, other medical disorders and the potential for development of dependency. A decrease in the weekly consumption to below 14 drinks total is recommended to eliminate this risk factor. A "drink" equals one 12 oz. beer or a 1-1/2 oz. measurement of distilled beverage at 80 proof.

You also report avoiding the use of mood altering medication on a regular basis. This is also a very positive aspect in this area.

Fig. 10.

IV. STRESS

"Stress" is the reaction of your body to demands made upon it—including both emotional and physical demands. Increased heart rate, changes in blood pressure, or changes in body temperature are some examples of your body's "stress reactions."

Moderate stress is normal and is *not* something to avoid. Too much stress, however, can upset the body's balance and have negative effects on your health. Repeated, excess stress can lead to such problems as peptic ulcers, hypertension, tension headaches, and a variety of other illnesses.

● Stress Caused by Life Events

Stress reactions can be caused by the daily pressures of home or work. They can also be caused by major changes or events happening in your life.

Many major life events occuring within a short period of time can increase your risk of illness or other stress problems. We think this happens because adjustment to any major change is a stress. A life event can be either "desirable" or "undesirable" to you and still produce a stress reaction.

Your tolerance for stress is a very individual matter. If your "Stressful Life Event" scores are high, that may indicate that you need to pay extra attention to sound health care practices (relaxation, "time out," good nutrition, exercise, etc.).

● Indications of Your Sensitivity to Stress

Higher levels of anxiety and tension may be signs that you are currently sensitive to stress. Physical symptoms or complaints can also signal an increased sensitivity to stress.

Methods of relaxing and coping with stress can prevent stress related illnesses. You can build up your overall "stress fitness."

Increasing your awareness of the sources of pressure in your life and understanding the way you react to stress can help you better manage your stress.

● Your Stress Recommendations:

You presently score within a slightly higher range on stressful life events over the past year. This means that you have been experiencing a fairly high level of recent change demands. Life events associated with change may be desirable or may be undesirable, but do require adjustment. This score reflects an estimate of current transitional stress and does not consider additional daily, cumulative pressures.

There was no way to evaluate your current stress sensitivity because this section of the questionnaire was left blank. You do not, however, currently show any tendency to convert stress into physical ailments.

You indicate that you regularly participate in sports to relax. This is an effective stress management strategy and can be supplemented by participation in additional restful activities such as hobbies or outside interests. During periods of higher demand and pressure you can also benefit by paying more attention to relaxing breaks from routine and vacations.

Fig. 11.

V. Your "HEALTH POTENTIAL AGE"

Your Health Potential Summary does not predict precise life expectancy for you personally. It is, instead, a measure that applies to people of your sex, age, race, and habits, in general. You can use the information provided to assess your current lifestyle habits or risk factors as they relate to your general health. You have the *potential* for improving your health by taking steps to reduce your risk factors.

● Your "Adjusted Health Age"

"Health age" is a new way of summarizing your present state of health developed by the National Centers for Disease Control (CDC). Estimates of life expectancy and health potential are calculated based on your age, sex, race and present lifestyle habits.

Your "Actual Age" is your true age.

Your "Appraised Health Age" results from a calculation that reflects your "age" in terms of health characteristics. The lower your health risks are, the lower is your appraised age, and vice versa. If your Appraised Age is about the same as your Actual Age, your Health Potential is "average," or about the same as for other people of your sex and age group.

"Achievable Age" is a lowered risk or "Appraised Age" you can achieve if you improve lifestyle habits as recommended in your Health Potential Summary.

● Your Risk Factor Recommendations:

If you reduce down from your reported weight of 195 to your ideal weight of 157, your risk of dying from heart disease and diabetes will be reduced and you will decrease your appraised age by 1.6 years.

If you stop drinking alcohol, or limit your consumption (less than 3-6 drinks per week) and do not drive after drinking or ride with a driver who has been drinking, your risk of dying from motor vehicle accidents, cirrhosis of the liver, and pneumonia will be reduced and you will decrease your appraised risk age of 0.7 years.

If you wear seat belts all of the time, your risk of dying from a motor vehicle accident will be reduced and you will decrease your appraised risk age by 0.5 years.

If you have a yearly procto (rectal examination) after age 40, or 3 negative stool tests for occult blood, your risk of dying from cancer of the large intestine and rectum will be reduced and you will decrease your risk age by 0.1 years.

If you follow the recommendations included in this report for beginning or continuing an exercise program, your risk of dying from heart disease will be reduced and you will decrease your appraised risk age by 1.4 years.

Fig. 12.a

Health Potential Summary

SUMMARIZING HOW YOUR CURRENT LIFESTYLE AFFECTS YOUR HEALTH POTENTIAL:

NAME: REAL EXAMPLE OF PATIENT "X"  DATE: January, 1982
PHYSICIAN: Dr. Cashman  PROGRAM:

I. NUTRITION

Fat as Percent of Calories

Polyunsaturated/Saturated Fat Ratio

Dietary Cholesterol

Salt (Sodium)

Percent Body Fat  FEMALE:

MALE:

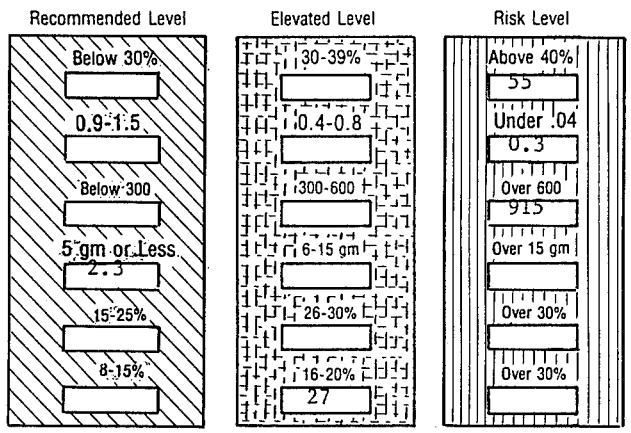

II. EXERCISE

RISK FOR CARDIOVASCULAR DISEASE

Exercise ON-THE-JOB

Exercise OFF-THE-JOB

◊ TOTAL Exercise

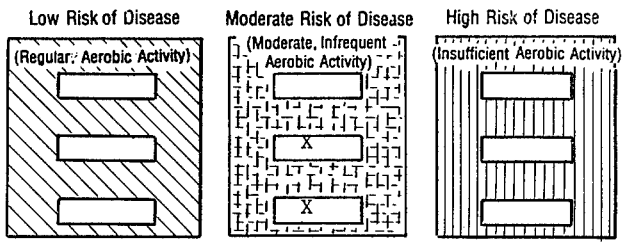

III. CONSUMPTION OF Tobacco, Alcohol, Drugs

TOBACCO

ALCOHOL*
*1 Drink = 12-oz beer, 4-oz wine or 1% oz distilled beverage.

MOOD-ALTERING DRUGS
(Not prescribed by your physician for a specific condition for a limited period of time)

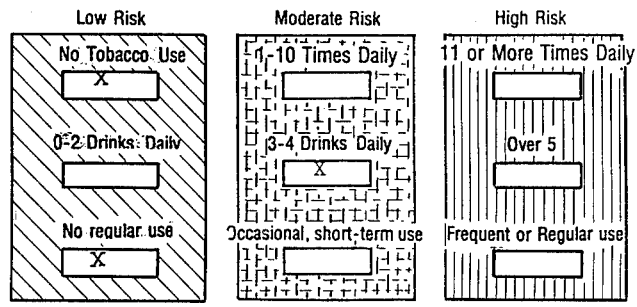

Fig. 12.b

IV. STRESS

STRESSFUL LIFE EVENT SCORES: (Within the Past Year:)

| 61 family | 0 work | 0 social |
| 53 personal | 0 legal | 0 leisure |
| 0 health | 69 financial | 0 spiritual |

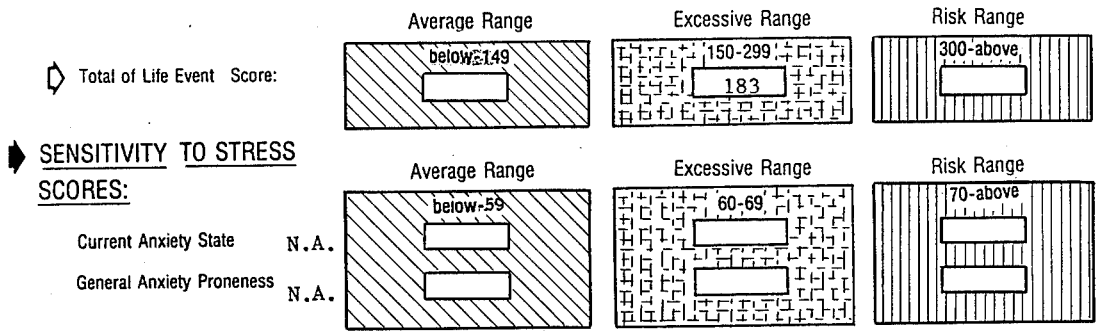

▷ Total of Life Event Score:

▶ SENSITIVITY TO STRESS SCORES:
  Current Anxiety State    N.A.
  General Anxiety Proneness  N.A.

V. Health Potential Summary: Your Present Health— —Expressed in "Adjusted Age"

Below are three "ages" we have computed for you from information you provided for this report:

- Your ACTUAL AGE is the total number of years since you were born: 45

- Your APPRAISED AGE suggests how your present health makes you "older" or "younger" than your actual age: 46.5

- Your ACHIEVABLE AGE shows how you can change "Appraised Age" by improving your health habits: 40.4

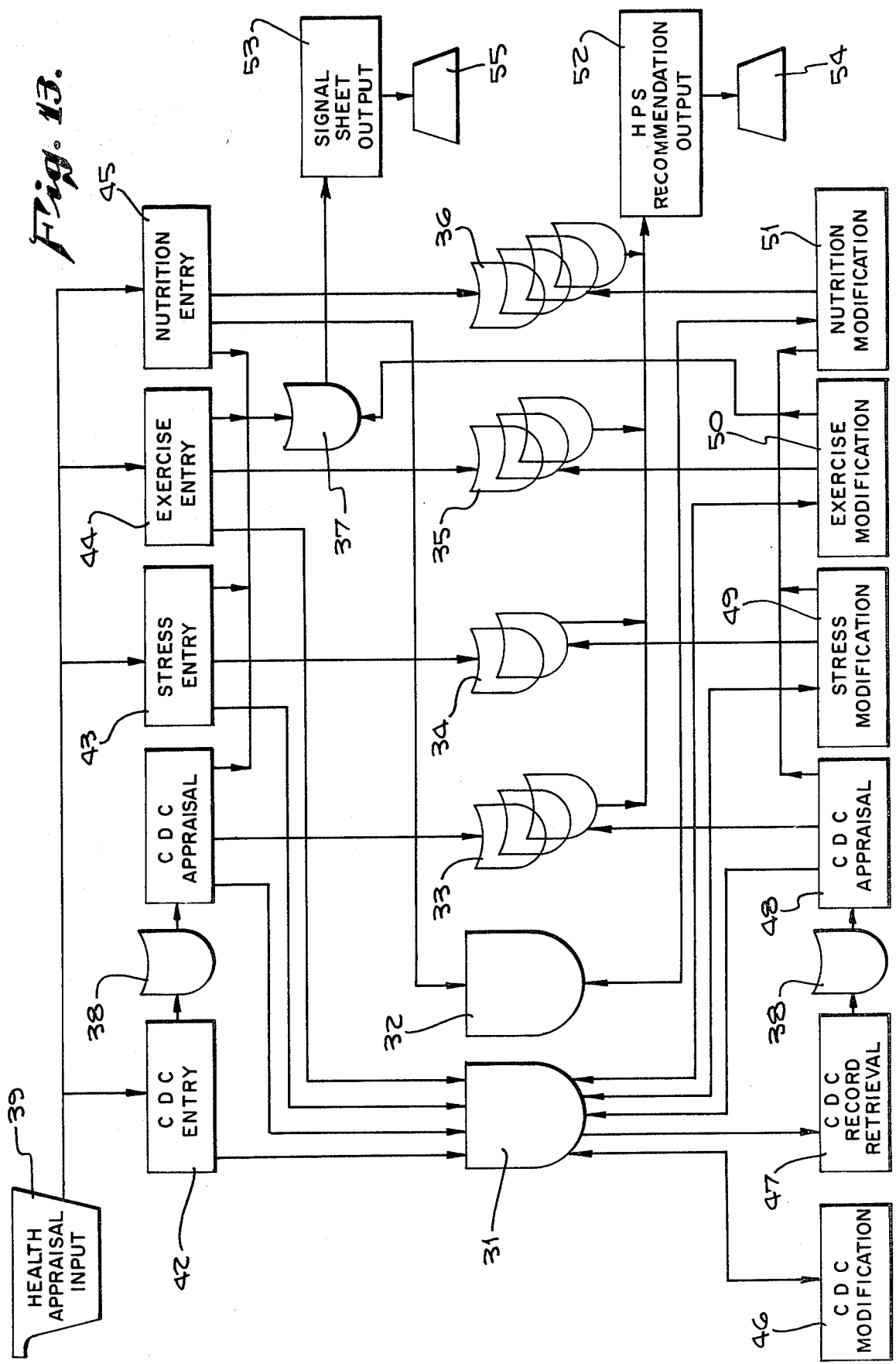

HEALTH POTENTIAL SUMMARY AND INCENTIVE SYSTEM

The invention relates to a system giving rise to a method for generating a summary in the form of commentary and recommendations with respect to the health of a subject, which results further in an abbreviated resume, visually accented in some fashion, so as to draw the subject's attention not only to the subject's physical condition, but an improved condition which could be achieved by making sundry suggested changes in a person's life-style. The arrangement of the system is, moreover, one which not only is as complete as good practice permits, but also one which can be effectively used for the benefit of a relatively large number of subjects in a fashion capable of producing the commentary, recommendations and resume relatively quickly, largely automatically, and with virtually a minimum need for professional consultation either before the system is applied to the subject's needs or after the commentary, recommendations and resume have been completed.

Various techniques have been applied heretofore, having for their purpose to change irrational and health-threatening behaviors. Two inversely positioned paradigms or philosophies have reigned. One is that the physician is in control of the communication and, in effect, orders his patients to act in a prescribed fashion. Many studies which have been made to uncover the causes of what is called low patient compliance with doctor's orders show that most people have not, for example, lost weight, stopped smoking, started exercising, etc., in response to having had their doctor tell them to do so, in a general abstract or even an authoritative way.

The opposite paradigm for changing individual health behavior may be called the public health or educational approach. This approach posits that it is possible to communicate in an education-like style with individuals to let such individuals know the consequences of their present behavior in a way that best combines individualized data with machine mass processing capability. Health risk appraisal programs currently in vogue stem primarily from the public health educational approach and leave the personal physician outside of the educational loop.

In addition to health advisory publications, various of which include the consequences of good and bad health habits by means of tables and charts, some health promotion institutions have inaugurated programs of questionnaires and the resulting tabulation of information, ultimately returned to the subject in the guise of recommendations. Many of these are available from the Office of Health Information, U.S. Department of Health and Human Services. Typical of some of these is the publication "Health 80's for Hospitals" by Medical Datamation. This program features a somewhat extensive questionnaire respecting health habits which results in the production of a computerized response.

Another is a questionnaire promulgated by the Institute for Personal Health, with a somewhat complex arrangement for rated answers to each of the various questions which produces a report after being appropriately analyzed by an expert staff.

Another of more limited character appears in the form of a single sheet, two-page "Personal Risk Profile" prepared by General Health, Inc. Others also are available, usually directed to some specific factor influencing health.

Although such programs as have heretofore been available undertake to remedy sundry specific health conditions, they have been such that for large scale production there is too great a demand for individual analysis by a professional staff or, on the contrary too impersonal with respect to commentary and recommendations where such is derived from a computerized analysis. Little, if any, attention has been given to the problem of stimulating compliance on the part of the subject.

Typical of the approach heretofore taken has been to take some personal data on a given individual, and compare that data against other people in a normative data base who have had similar answers. Health expectations from that normative data base profile that most nearly matches the individual user's results have then been fed back to the user in such forms as chronological vs. health habits age, and with such extremely generalized recommendations for behavior changes as a recommendation that use of seat belts 75% of the time or more will increase the subject's odds for a longer life.

It is therefore among the objects of the invention to provide a new and improved system and method for health potential analysis directed to persuading a maximum number of subjects to make the maximum amount of positive, healthy, life-style change.

Another object of the invention is to provide a new and improved system and method for health potential analysis wherein the subject matter of the areas of inquiry are expanded in order to provide a more comprehensive variety of information for analysis.

Still another object of the invention is to provide a new and improved system and method for health potential analysis wherein a portion of the input upon which the analysis is based is predicated upon actual current dietary information and present exercise information, in addition to other more conventional items of information.

Still another object of the invention is to provide a new and improved system and method for health potential analysis laterally expanded with respect to the character of information which includes information respecting stressful life events in the subject's recent life.

Still further among the objects of the invention is to provide in a new and improved system and method for health potential analysis a means for cross-correlating the different expanded areas of inquiry and information so that commentary and recommendations to the subject directed to specific categories take into consideration conditions outside of such categories but which have an actual impact upon the commentary and recommendations given to the subject.

Further included among the objects of the invention is to provide a new and improved system and method for health potential analysis which includes a graphic persuasively presented resume in a manner such that the subject need have no knowledge or appreciation for computerized sophisticated recommendations but need only be capable of reading simple, layman-like language and figures, brought to the subject's attention in a graphic fashion which itself is formulated to have a persuasive effect upon the ultimate compliance of the subject.

Another object of the invention is directed to helping the subject understand the meaning of risk-taking in relation to personal behavior patterns and that how the person lives often determines how the person dies; which demonstrates through concepts of risk and achievable age the effects of risk taking, showing that individual risks not only add to but compound one another; which personalizes the life-style hazards to help the subject realize that such hazards can apply to the subject, which indicates by the commentary and recommendations the relative importance of life-style risks, thereby to enable the subject to choose which risks to eliminate; which by commentary and recommendations conveys a sense of urgency to help motivate the individual to make changes, and which provides a prospect and measure of reduced risk if certain bad habits are altered.

With these and other objects in view, the invention consists of the arrangement and combination of the various aspects of the system, serving as an example only of one or more embodiments of the invention, whereby the objects contemplated are attained, as hereinafter disclosed in the specification, and pointed out in the appended claims.

FIG. 1 is a schematic diagram of the computer program summary.

FIG. 2 is a reproduction of a portion of the health appraisal section of the questionnaire for the health potential summary.

FIG. 3 is a reproduction of a portion of the stress information section of the questionnaire.

FIG. 5 is a portion of the nutrition analysis section of the questionnaire.

FIG. 6 is a reproduction of the food diary form for one day of the food diary record.

FIGS. 7a, 7b and 7c are reproductions of portions of the nutrition section of resulting recommendations of the health potential summary.

FIG. 8 is a reproduction of a portion of the exercise section of the recommendations.

FIG. 9 is a portion of the non-nutrition intake section of the recommendations.

FIG. 10 is a reproduction of a portion of the stress section of the recommendations.

FIG. 11 is a reproduction of a portion of the health potential age section of the recommendations.

FIGS. 12a and 12b are reproductions of multi-color summary sheets of recommendations in the form of a compact resume.

FIG. 13 is a more detailed schematic diagram of the computer program showing the intermixing of program material.

Figure 4:
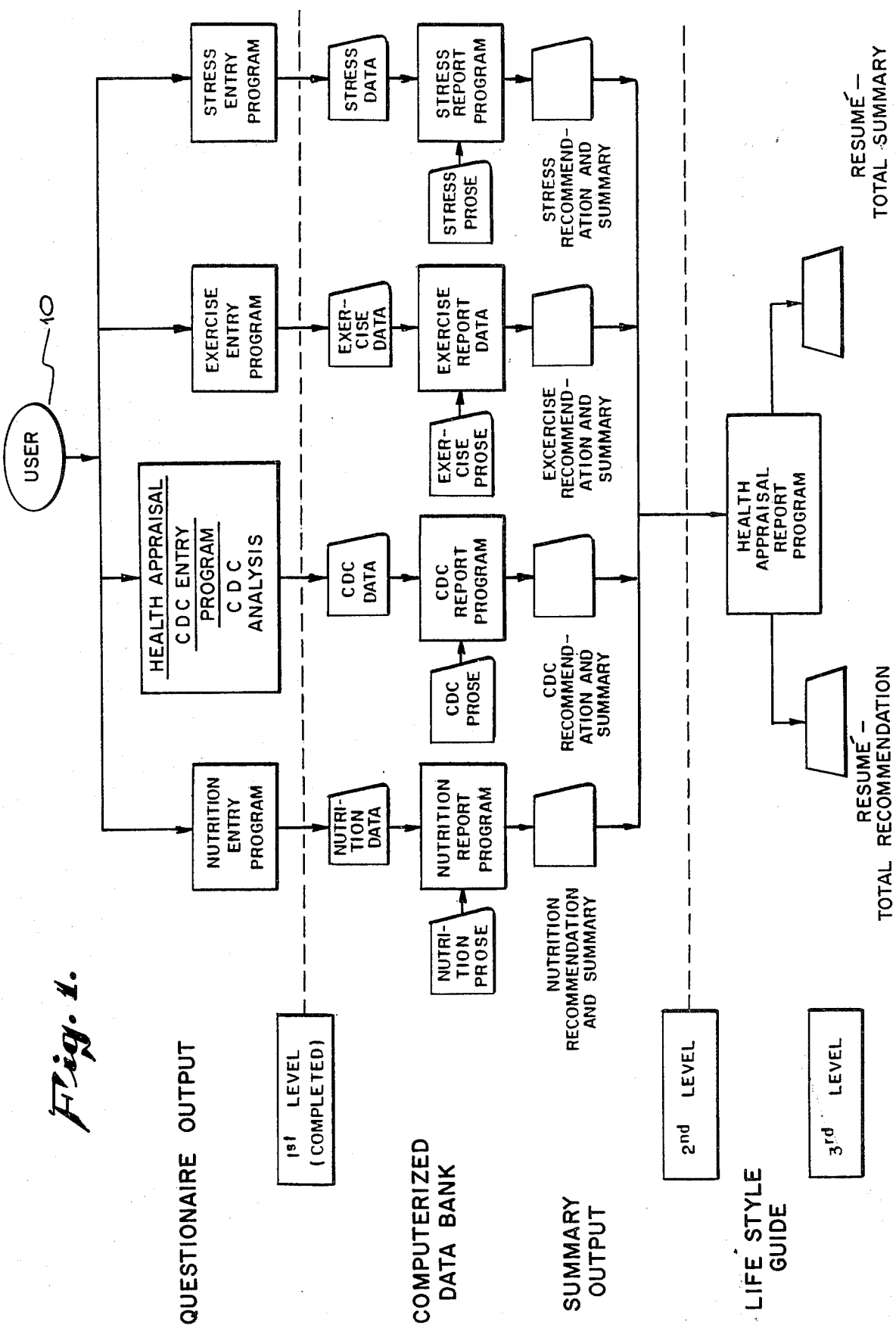
FIG. 4 is a reproduction of a portion of the exercise section of the questionnaire.

In an embodiment of the invention chosen for the purpose of illustration the method of preparing a health potential analysis involves employment of three different documents. These comprise a multi-page questionnaire, a multiple page printout of individual recommendations compared with typical recommendations, and a very abbreviated two-page resume of the recommendations. To bridge the process between collection of answers to the questionnaire and the reproduction of a set of recommendations, the method makes use of a data bank in which is stored a multiplicity of recommendations designed to fit as many as possible of circumstances which are likely to be made reference to by answers to the questionnaire, and a multiplicity of encoded "free language" extracted from answers to the questionnaire's exercise and nutrition sections. So that the information in the data bank may be properly called upon for reproduction, the items of information are keyed to what may readily be described as "scorebox" answers or combination of answers in the questionnaire, so that when the recommendations are printed on the subject's multiple page health potential summary recommendations they will be in a proper recommended order and at the same time relate personally to the subject's habits and life style.

The schematic diagram of FIG. 1, which is in effect a flow sheet of the sundry steps as they are taken, is a guide for introducing the information which has been collected about a subject or use to the data bank where it is sorted out and made use of in triggering imprintation of recommendations together with comment and "free language" at a properly prepared location in the health potential summary recommendations from which is extracted the resume of information. The result achieved by the resume is the substance of the recommendations which can be obtained with a moment of reading.

To collect the information on a particular subject or user, indicated by the reference character 10, use is made of a multiple page health potential summary questionnaire. The questionnaire consists of different parts, as for example page 11, identified as Part 1: Health Appraisal Questions, a portion of which is shown in FIG. 2. A second part of the health potential summary questionnaire exemplified by pages 12, 12' in FIG. 3, is identified as Part 2: Stress Information. Still another part of the health potential summary questionnaire identified as Part 3: Exercise Data, is exemplified by pages 13, 13' of FIG. 4. FIG. 5, which is devoted to Part 4: Nutrition Analysis, is exemplified by page 14.

Another unnumbered part of the health potential summary questionnaire, as exemplified in FIG. 6, consists of a Food Diary, page 15, for a succession of selected days, as exemplified particularly by day 1, as shown in FIG. 6. Still another part of the health potential summary questionnaire, not shown by way of printed example, is a part identified as Medical Records Data.

Of special note in providing answers to items in the health potential summary questionnaire is the box score depicted on the right of FIG. 2. Only 22 questions are pictured on pages 11, 11' of FIG. 2, out of a total number of questions which may number 35, 40 or even more. The questions in all instances are carefully selected as being questions the answers of which will be of appreciable significance in the achievement of an accurate and dependable result. The questions are also carefully phrased so that they can be effectively answered in a box score fashion.

Attention is directed to FIG. 2, page 11 where, for questions 1 and 2 a small box requires only a check mark for answer to the question, whereas for questions 3, 4 and 5 a larger box is selected where a selected numeral or figure is needed to answer the question.

A similar pattern is followed with respect to question 6, smaller boxes being provided where they need only to be checked and larger boxes provided where some selected figure must be chosen.

For a slightly different pattern of answering as shown for page 11', small boxes are provided for question 22, respectively applicable to a different number of hours of sleep, the span of which is proposed by the question. The balance of the group of questions illiciting health appraisal information, appearing on subsequent pages, are similarly set up for answer by way of a box score.

In illiciting stress information as depicted in FIG. 3, page 12 shows box scoring in a very slightly modified fashion. For the first list of 15 items of information, the boxes are in fact arranged for either a yes or no answer in the alternative, the answer being made by merely checking the proper box. For the lower set of information items on page 12' numbering eight in all in FIG. 3, a degree rated answer is required in accordance with a specified rate scale of four degrees. These are No. 1, meaning not at all; No. 2, meaning somewhat; No. 3, meaning moderately so; and No. 4, meaning very much so. The subject, or user need only place the appropriate numeral in the box as the box score. Additional catagories of emotional condition or feeling are also provided set up in a similar fashion.

In differentiating the categories, it should be noted that information for the upper category as depicted on FIG. 3 are items of information respecting circumstances which may have occured at any time, whereas the eight statements at the lower portion of FIG. 3 are concerned only with conditions at the moment of answering. Still another category can be information respecting feelings experienced as a general rule. Still another can be information respecting symptoms and complaints experienced by people generally, and experienced by the subject or user during a recent period as, for example, seven days. These are applied for example against a rate scale of 0, meaning not at all; 1, meaning a little bit; 2, meaning moderately; 3, meaning quite a bit; and 4, meaning extremely, the numerals being applied to the box in the form of a box score.

In view of the extremely wide variety of types of exercise which one user or another might enjoy, to the exclusion of most others, Part 3, illiciting exercise data information is set up with a multiplicity of suggestions. On this occasion a large box is provided for a numeral depicting the number of times the exercise was engaged in over the immediately preceeding two week period, followed by the length of time of the engagement. Here again, the answer is kept in simple form to the extent possible by the character of information needed so as to provide the answer in box score fashion.

Since nutrition is an extremely important factor in any health potential analysis program, the method here under consideration provides for supplying nutrition information in two distinctly different ways. As depicted by page 14 of FIG. 5, Part 4: Nutrition Analysis, first gives an example as to how the information should be given. Thereafter, on the left side of page 14 and succeeding pages, is listed virtually all of the customary food items which the average person is most likely to consume. To capture the answer in the quickest and easiest way, and in a manner such that the information can ultimately be fed into a data bank, suggestions are made for consumption daily, weekly or monthly, associated with the number of times for the selected period of the answer. Coupled with the manner of answering as described, the Part 4: Nutrition Analysis may conclude with questions such as whether or not the user is following a special diet; whether taking vitamins or food supplements; where foods are prepared as, for example, whether at home or restaurant prepared; and whether or not some foods are productive of allergies or not eaten for other special reasons.

In addition to the somewhat generalized analysis information for which is provided in the manner of FIG. 5, provision is also made for a specific food intake diary, as depicted by page 15 in FIG. 6. The diary for one day is depicted whereas the system contemplates diaries for additional days, preferably a minimum of three days and possibly additional days. As a guide for the subject or user in supplying the information requested on page 15, a dietary sequence is suggested which would in most instances be typical. The time is noted, the place noted, specific foods identified, method of preparation depicted, and especially the amount of intake of each specific food item. The system contemplates a detailed item by item summary of all foods and circumstances and quantities of consumption for each meal or snack for a specified number of days. Such days may be in sequence or scattered at intervals over a selected period of time. The diary is intended as a realistic record food intake and not one wherein eating habits have been reformed or qualified, circumstances which would impair the accuracy of the ultimate summary and recommendations.

The information respecting a particular subject or use now having been accumulated in written form in the health potential summary questionnaire is then ready for analysis where analysis may be required. To the extent that individual analysis may be needed in view of the character of the answers in the questionnaire, trained personnel following a procedural routine can be made use of. In conformance with the system, the analyzed subject matter together with the box score information is then appropriately fed into the computerized data bank following in general the schematic flow diagrams of FIG. 1.

For a more comprehensive understanding of how the varied items of information are cross-related to influence the recommendations, reference is made to the schematic diagram of FIG. 13, taken in company with identifying designations as follows:

31=Data base containing encoded data for center of disease control (CDC), stress and exercise
32=Data base containing encoded data for nutrition
33=Files containing paragraph results for CDC
34=Files containing paragraph results for stress
35=Files containing paragraph results for exercise
36=Files containing paragraph results for nutrition
37=File containing information for signal sheet
38=File containing information for CDC appraisal program
39=Source input document for HPS entry program
42–51=Programs (as specifically noted)
52=HPS recommendation output
53=Signal sheet output
54=Final recommendations output
55=Final signal sheet output As depicted in FIG. 13, the health appraisal input, source input document for HPS entry program 39, comprises answers to the questionnaire previously made reference to, FIGS. 2 through 6, inclusive. This information is fed respectively to the computer programs identified as CDC Entry 42, Stress Entry 43, Exercise Entry 44, and Nutrition Entry 45. From here the information is fed variously, as indicated by the arrowed lines of FIG. 13. Upon being evaluated in accordance with a prearranged program, the information results in two outputs, namely, a health potential summary (HPS) recommendation output 52, and a signal sheet output 53. The HPS recommendation output 52 results in a printout 54 which is the material depicted by way of example in FIGS. 7a through FIG. 11, inclusive. The signal sheet output 53 results in a printout 55 exemplified by the previously described printout sheets depicted by way of example in FIGS. 12a and 12b.

In making the transition from the health appraisal input 39 to the two printouts 54 and 55, that portion of the health appraisal input represented by the center for disease control entry (CDC) 42 progresses in two directions, namely, to a modified center for disease control (CDC) appraisal 48 and to a data base 31 containing encoded data for CDC, stress and exercise. Additional modification for this information is possible as represented by the CDC modification 46 and CDC record retrieval 47, CDC information files 38 taken again with the CDC appraisal 48 for correction of individual records.

The ultimate appraisal of the CDC information is transferred to two outputs. For the signal sheet output 53 and printout 55 the information is first put through a signal sheet information evaluator or file 37, where it is compared and evaluated with respect to other items of information. Comparable CDC information travels a different route to the HPS recommendations output 52 and its corresponding printout 54. In the last instance the information is modified by information in a file 33 containing paragraph results for CDC. Additional modification also is derived as needed from the CDC modification program 46. Modification programs are to modify or change incorrect encoded data for individual records.

Stress information from the health appraisal input 39, after traveling to a stress entry program 43, is programmed comparably. Some information passes directly to the file 37 containing information for the signal sheet output 53 and printout 55. Other portions travel in part to the data base 31 and in part to a file 34 containing paragraph results for stress. Stress information entering the data base 31 undergoes modification if necessary, the result of which is transmitted to the same file 34, after which the paragraph information is communicated to the HPS recommendation output 52 and ultimately its corresponding printout 54. An example of the printout result can be noted in FIG. 10.

Exercise information is treated comparably. After the exercise entry 44, the exercise information is stored in the data base 31 and in part in file 37 containing information for the signal sheet output 53. The exercise information for the data base 31 undergoes modification, if necessary, by the exercise modification program 50, after which, together with exercise information traveling directly to the file 35 containing paragraph results for exercise, the paragraph results are transmitted to the HPS recommendations output 52 and its corresponding printout 54. An example of the results can be noted by the information on FIG. 8 previously made reference to.

Nutrition information from the health appraisal input 39 is correspondingly treated after reaching the nutrition entry 45. As previously described, the nutrition entry is stored in part in file 37 containing information for the signal sheet output 53 and its printout 55. Other nutrition information is stored in data base 32 containing encoded data for nutrition, modified if necessary by a nutrition modification program 51. The nutrition information, upon passing to the file 36 containing program results and paragraphs for nutrition, is then passed to the HPS recommendations output 52 and its corresponding printout 54, together with nutrition information directly from the nutrition entry 45 which travels a corresponding route.

It should be appreciated from the foregoing resume of appraisal of the varied items of health appraisal input that the HPS recommendations output for each item in turn is affected and modified systemmatically by other items and information and not evaluated independently. The intermix of evaluation additionally results in a printout such as depicted in FIG. 9, having to do with the effects of alcohol, tobacco and drugs.

Of special consequence is information with respect to the manner in which handling of the various programs affects age. Although chronological age is a printout merely of information given in the health appraisal input 39, the appraised age printout is derived from an evaluation of the various different items of information which have been passed through the evaluating process. As an inducement to abide by a recommended improved program, the printout of achievable age, also derived from an evaluation of information of various kinds, is shown in its relationship to actual age and appraised age, especially as a relative age younger than the others. Such an evaluation is of special value to persons of more mature years. In this context the printout 55 depicted, for example, in FIGS. 12a and 12b, is of special importance to the program as a whole, especially when taken together with the other printout information of health potential summary (HPS) recommendations.

The ultimate objective is the printouts from the data bank of individual health potential summary comments and recommendations in substantially the form depicted in FIGS. 7a through 11.

In FIG. 7a depicting page 20 of a multi-page document identified as Health Potential Summary Recommendations, nutrition recommendations appear, and in a manner differentiating between a male and female user. Nutrients of greatest consequence are listed in company with a recommended amount of intake, where applicable, followed by the specific average daily consumption of that particular user, taken from information supplied by the user in the questionnaire. The information is set up on a comparative basis so that it is immediately apparent to the user whether or not the average consumption falls within or outside of the recommended amounts. On a succeeding page 21, as depicted in FIG. 7b, more comprehensive recommendations with respect to fat consumption are given in narrative fashion. The comments are spaced adequately to allow room on the right hand side for the specific recommendations applicable to the individual user to whom the recommendations are directed. Here also the recommendations are in narrative form with specific numerical quantities and percentages interposed, along with examples of foods extracted from free language tables predicated upon nutrition information actually supplied by the three-day food diary and derived from the encoded questionnaire.

The same pattern is followed with respect to percent body fat recommendations, and the nutrition recommendations applicable to the user based upon information from the questionnaire and related to the user's weight and height.

Proteins may be treated in a comparable fashion. Also on page 22 shown in FIG. 7c, a vitamin and mineral intake is recommended at the left of the page followed on the right of the page with specific recommendations to the user derived from information supplied by answers of the user to the user's questionnaire. The specific recommendations noting a deficiency in milk intake, for example, recommends eliminating the deficiency by increasing the servings of milk, but using milk of a lower fat content than the user indicated on the questionnaire.

Recommended salt intake is compared in a comparable fashion with the individual's sodium equivalent intake, with accompanying recommendations.

A departure from conventional recommendations for programs of this kind is made use of on page 2, FIG. 8. After narrative recommendations respecting flexibility and cardiovascular endurance, specific recommendations are given applicable to the user predicated upon the exercise information actually supplied in answer to the questionnaire. By tying the exercise recommendations to the user's choice of exercise, golf for example, attention of the user is captured to a greater degree and focused upon a revision of exercise habits that can be most easily accomplished. Additional exercise items, such for example as muscular function, can be presented as a general recommendation, having coupled with it, in the space provided toward the right, following the same pattern as page 22, a specific recommendation for the user prompted by his report in answer to the questionnaire.

As is always important, recommendations with respect to normal body weight may be injected into the health potential summary recommendations followed by specific reference to the weight condition and weight forming habits of the user, as revealed by answers to the questionnaire. Because of the potential health hazards of overconsumption of alcohol, tobacco and drugs, page 24 as shown in FIG. 9 devotes appreciable space to general recommendations, on the left of the page under the caption "a caution", with available space to the right of the page having imprinted therein an evaluation of the user's use, for example, of alcohol. The phraseology of the specific recommendations is such that quantities can be readily inserted which have a direct relationship to the user's report as appearing in answers to information in the user's questionnaire.

Much the same general approach is made use of in recommendations respecting page 25 devoted to stress as depicted in FIG. 10. General recommendations appear on the left. Space is provided on the right wherein the specific recommendations applicable to the user as evidenced by answers to the questionnaire are imprinted.

What is significant by way of example on page 25 where the specific stress recommendations are made is that the recommendations stem not only from the stress information given by answers to the questionnaire but exercise information from a separate and different part of the questionnaire. In providing an overall health potential summary, one of the features of the present method is to cross relate information given in different parts of the questionnaire so that the specific recommendations will not relate solely to answers given in one part only. By having adequate information stored in the data bank applicable to cross related topics, the cross relationship of recommendations is made possible.

Of singular importance in the health potential summary recommendations is page 26, shown in FIG. 11, on the topic health potential age. On most occasions the information and recommendations heretofore discussed tend to be accepted readily even by the serious and well-intentioned users, but in a manner tending to be accepted as a matter of course. If the user's health and health potential age is to be improved, some extra inducement to follow the recommendations becomes highly beneficial and much to be desired. This is particularly to be desired under circumstances where a health improvement program is encouraged by an employer, willing to meet the expense in return for the benefits of improved health of all employees concerned. The standard recommendations respecting relationship between actual age, appraised age and achievable age are important not only as a general guide but especially important when applied to the particular user. Specific items relating to the user's health habits are accordingly printed out in the form of recommendations coupled with their relationship to age measured in years and fractions of years. Each element of a number of elements is spelled out separately in a descriptive fashion and coupled with a measure of years. Although the innumerated prospective decrease in appraised risk age are averages at best, the figures are nevertheless dependable figures taken from data accumulated by reliable sources over a period of time.

To provide a still further inducement to the user to abide by the recommendations, and bearing in mind that information which is of necessity reported in some particular over numerous pages, a sharp graphic and concise resume is especially stressed. This is the resume depicted on pages 27 and 28 respectively of FIGS. 12a and 12b. On page 27 are depicted the categories of nutrition, exercise and consumption of tobacco, alcohol and drugs. For nutrition only the salient important nutritive items are listed. Immediately to the right is a rectangular box, color accented for green showing recommended levels of the chosen nutrients. Recommendations are in numbers because numbers are easily read and remembered. The user's salt intake in the example is printed in the salt box score as less than the recommended level.

Elevated levels for the same nutrients are also listed in a rectangular box immediately to the right of the recommended level box wherein the elevated level box is accented for the color yellow. On this occasion where the user's percent body fat happens to fall within the elevated level, the user's percentage, as derived from the answers to the questionnaire, is imprinted as twenty-seven percent (27%), slightly over the elevated level percentage range. Still further to the right in the rectangular box, color accented for the color red are depicted risk levels for the chosen nutrients. The remaining information for that particular user is imprinted in numerical quantities at the appropriate locations for the nutrients within the risk level. Fat is identified as being fifty-five percent (55%) which is over the forty percent (40%) risk level. The fat ratio is shown as being substantially over the risk level of 0.04. Dietary cholesterol is identified as 915, substantially over the risk level of 600.

The same general pattern is likewise followed for both exercise and consumption of tobacco, alcohol and drugs where the low risk is color accented for green, moderate risk color accented for yellow, and the high risk color accented for red. Although these color sequences have been chosen because green means acceptable, yellow a warning, and red a danger signal, other means of depicting relative accents could be chosen.

Of express importance from the point of view of providing incentive for improving health potential are the predictions and information graphically depicted as page 28 and as shown in FIG. 12b. At the bottom of the page in a space specially provided is printed the actual age of the user taken from information supplied by the user. Following that is a figure for the user's appraised age. As shown, this is a figure older than the actual age because of the health habits reported by the user in answer to the questionnaire. Following the appraised age is an indication for the user's achievable age, namely, the achiever's age resulting from good health habits, should the user discontinue some objectionable health habits and employ in the aggregate other desirable health habits. The achievable age is the sum of average decrease in appraised risk age, taken from certain risk age factors such as those of FIG. 11 subtracted from the user's appraised age. Since good health is so commonly associated with the vigor of youthfulness, the achievable age figure is graphically presented and compared with the other age figures as an important inducement for the user to improve the user's health habits.

Although the health improvement inducement program is graphically directed to the individual as the result of the health potential summary recommendations and resume, the system also contemplates a program of activity with features directed expressly to the general improvement needs indicated by deficiencies illuminated in the health potential summary.

While a particular embodiment of the present invention has been shown and described, it will be obvious to those skilled in the state of the art that changes and modifications may be made without departing from the invention in its broader aspects, and therefore, the aim of its appended claims is to cover all such changes and modifications as fall within the true spirit and scope of his invention.

Having described the invention, what is claimed as new in support of Letters Patent is as follows:

1. The method of preparing a health potential analysis for a human subject by use of imprinted material and a data bank, said method comprising establishing a plurality of categories of health related information, preparing a questionnaire comprising a set of information inquiries for each category wherein the inquiries are subject to score box responses of the character of yes, no, unanswered, or answered by a character according to a graduated scale, subjecting the questionnaire to responses by the human subject and preserving the responses thereto, storing in the data bank an inventory of health implementing commentary and recommendations, preparing a set of instructions to direct commands to the data bank wherein the instructions are keyed to the score box responses, preparing an analysis in the form of a multiple part health potential summary report having for a first part a series of preprinted recommendations respecting health practice for the respective categories and for a second part spaces to accept information, preparing a life-style resume document on which is depicted sets of visually accented read-out displays at visually adjacent locations for showing respectively recommended health practice, moderately exceptional health practice and high-risk health practice for said categories, and feeding commands to the data bank to effect a print-out of subject directed commentary and recommendations on respective spaces of said second part of the summary report at locations visually adjacent related preprinted recommendations.

2. A method of preparing a health potential analysis according to claim 1 including establishing as said categories a nutrition category, an exercise category, an alcohol, tobacco and drug consumption category, and a stress category.

3. A method of preparing a health potential analysis according to claim 2 including cross-correlating in said instructions responses from a multiple number of said categories on the questionnaire.

4. A method of preparing a health potential analysis according to claim 2 including establishing in said nutrition category a set of inquiries directed to actual daily food intake.

5. A method of preparing a health potential analysis according to claim 4 wherein said daily food intake covers more than two days in a weekly sequence.

6. A method of preparing a health potential analysis according to claim 2 including establishing in said nutrition category a set of inquiries directed to food frequency intake.

7. A method of preparing a health potential analysis according to claim 2 including establishing a medical records category in the questionnaire.

8. A method of preparing a health potential analysis according to claim 1 including establishing a health potential age category in the health potential summary report.

9. A method of preparing a health potential analysis according to claim 8 including supplying recommendations and commentary for said health potential age category comprising information respecting appraised health age and achievable health age compared with actual age.

10. A method of preparing a health potential analysis according to claim 9 including showing ages in numerical time intervals in said visually accented read-out displays.

11. A method of preparing a health potential analysis according to claim 1 including showing said visually accented read-out displays as windowed block representations.

12. A method of preparing a health potential analysis according to claim 11 including showing said visually accented read-out displays in respectively different colors.

13. A method of preparing a health potential analysis according to claim 1 wherein said graduated scale is a numerical scale.

14. The method of preparing a health potential analysis according to claim 1 including imprinting on said life-style resume document at the corresponding set of said visually accented read-out displays, a separate abbreviated resume of the commentary and recommendations arranged according to a graduated scale.

* * * * *